United States Patent [19]

Nösberger

[11] Patent Number: 4,772,718

[45] Date of Patent: Sep. 20, 1988

[54] PROCESS FOR PREPARING 5-CYANO-4-METHYL-OXAZOLE

[75] Inventor: Paul Nösberger, Birsfelden, Switzerland

[73] Assignee: Hoffmann-La Roche Inc., Nutley, N.J.

[21] Appl. No.: 922,596

[22] Filed: Oct. 24, 1986

[30] Foreign Application Priority Data

Nov. 1, 1985 [CH] Switzerland ............... 4710/85

[51] Int. Cl.$^4$ .......................................... C07D 263/44
[52] U.S. Cl. ......................................................... 548/236
[58] Field of Search .................................. 548/215, 236

[56] References Cited

U.S. PATENT DOCUMENTS

| | | | |
|---|---|---|---|
| 2,200,734 | 5/1940 | Arnold et al. | 558/311 |
| 2,203,861 | 6/1940 | Deem et al. | 558/310 |
| 2,435,553 | 2/1948 | Bruson et al. | 558/457 |
| 3,845,094 | 10/1974 | Angstadt | 548/236 |
| 4,179,642 | 12/1979 | Olivé | 558/318 |
| 4,234,509 | 11/1980 | Billenstein | 558/312 |
| 4,255,584 | 3/1981 | Hoffmann-Paquotte | 548/236 |
| 4,482,503 | 11/1984 | Hofmann | 558/312 |

FOREIGN PATENT DOCUMENTS 822702 9/1969 Canada .
1542065 3/1979 United Kingdom .

OTHER PUBLICATIONS

J. Organic Chemistry 46, 754–757 (1981).
Japanese Patent Publication (Kokai) No. 113,752/1981–Derwent Abstract and English Language Translation.
Japanese Patent Publication (Kokai) No. 13,889/1972–Derwent Abstract.
Japanese Patent Publication (Kokai) No. 39,023/1972–Derwent Abstract.
Japanese Patent Publication (Kokai) No. 1649/1973–Derwent Abstract.
Japanese Patent Publication (Kokai) No. 2966/1975–Derwent Abstract.
Japanese Patent Publication (Kokai) No. 2967/1975–Derwent Abstract.
Japanese Patent Publication (Kokai) No. 82,646/1974–Derwent Abstract.
J. Synthetic Methods (Thielheimer)–Abstract No. 77837U.

*Primary Examiner*—Donald G. Daus
*Assistant Examiner*—Mark W. Noel
*Attorney, Agent, or Firm*—Jon S. Saxe; Bernard S. Leon; Richard J. Mazza

[57] ABSTRACT

A process for the manufacture of 5-cyano-4-methyl-oxazole which comprises reacting a 5-(lower alkoxycarbonyl)-4-methyl-oxazole with ammonia in the gaseous phase, in the presence of a zirconium oxide or hafnium oxide catalyst.

14 Claims, No Drawings

PROCESS FOR PREPARING 5-CYANO-4-METHYL-OXAZOLE

BACKGROUND OF THE INVENTION

The present invention is concerned with a novel process for preparing 5-cyano-4-methyl-oxazole, which is an important intermediate in the manufacture of pyridoxine (vitamin $B_6$).

This oxazole derivative has, before now, been manufactured by reacting 5-carbamoyl-4-methyl-oxazole with phosphorus pentoxide while heating. However, this process is associated with certain disadvantages, for example, a relatively low yield, attributable to carbonization which occurs very readily.

An improvement for this process comprises carrying out the reaction of the 5-carbamoyl-4-methyl-oxazole with the phosphorus pentoxide in the presence of a solvent, namely quinoline (see U.S. Pat. No. 3,222,374). This process also has disadvantages, particularly, instability observed under reaction conditions, a disagreeable odor, and detrimental effects on health of quinoline. Further, the procedures for the regeneration of quinoline and for converting products which are formed from the required phosphorus pentoxide into ecologically harmless products are costly and burdened with technological problems. Moreover, both quinoline and phosphorus pentoxide are expensive and scarce raw materials.

Another process for the manufacture of 5-cyano-4-methyloxazole comprises reacting 5-carbamoyl-4-methyl-oxazole with a lower alkanecarboxylic acid anhydride and subjecting the reaction mixture or the 5-(N-lower alkanoyl-carbamoyl)-4-methyl-oxazole isolated therefrom to pyrolysis. The final pyrolytic step has, however, certain disadvantages, such as, the necessity for working at high temperatures, problems with the materials from which the reactor is constructed, and the formation of byproducts which are difficult to recycle.

DESCRIPTION OF THE INVENTION

The present invention provides a process which enables 10 5-cyano-4-methyl-oxazole to be prepared in a simple and economical manner, by which the above-mentioned disadvantages of the known processes do not occur and the desired 5-cyano-4-methyl-oxazole is obtained in high yield and in good quality. This is achieved by starting from a 5-(lower alkoxycarbonyl)-4-methyl-oxazole and ammonia and carrying out the reaction of the starting materials in the gaseous phase and in the presence of a zirconium oxide or hafnium oxide catalyst, but not isolating and separately treating the 5-carbamoyl-4-methyl-oxazole formed as the intermediate.

As lower alkoxycarbonyl groups in the starting materials of this process there can be used, in particular, groups in which the alkoxy moiety contains up to 6 carbon atoms and is straight-chain or branched. The lower alkoxycarbonyl group is preferably ($C_{1-3}$-alkoxy)carbonyl, especially ethoxycarbonyl.

The zirconium oxide or hafnium oxide catalyst can be present in essentially pure form, that is, undiluted, or it can be mixed with an inert material or affixed to a carrier material, that is, diluted. Examples of suitable inert materials or carrier materials are aluminum oxide and aluminum silicate. Aluminum oxide is the preferred carrier material. Where the catalyst is diluted, then the amount of catalyst conveniently amounts to about 5 to 30 weight percent of the total amount. The catalyst is, however, preferably used in undiluted form. In each case the specific surface of the undiluted or diluted catalyst preferably amounts to at least 10 $m^2/g$. The best results are achieved by using undiluted catalysts with specific surfaces in the range of 10 to 40 $m^2/g$ or diluted catalysts with specific surfaces in the range of 10 to 90 $m^2/g$ (depending on the density of the accompanying material used).

The catalysts which are used in accordance with the 10 present invention are commercially available or can be produced readily in a manner known per se, for example, by precipitation from an aqueous solution of zirconyl or hafnium oxychloride with aqueous ammonia, filtration, washing with water, drying, pulverization, sieving, tabletting and calcination, e.g., at about 500°–800° C. Where the catalyst is to be diluted, the combination with the inert material or carrier material is effected at any stage of such a process, although no later than immediately prior to tabletting. The method used for the production and pre-treatment of the undiluted or diluted catalyst influences, inter alia, the value of the specific surface and at the same time the catalytic properties.

The most convenient amount of catalyst which is to be used can be determined readily by those skilled in the art. It depends, in particular, on the amount of starting materials used, the reaction temperature and the form and size of the reactor.

The reaction of the 5-(lower alkoxycarbonyl)-4-methyl-oxazole with ammonia in accordance with the invention is conveniently effected with an excess of ammonia, with the molar ratio of ammonia:oxazole being at least 1.5:1, and preferably 5:1 to 10:1.

Further, the reaction is conveniently effected in a temperature range of about 230°–400° C., preferably at temperatures between about 260° C. and about 350° C. With respect to the pressure under which the reaction is carried out, for technical and economical reasons the reaction is preferably effected under atmospheric pressure.

The 5-(lower alkoxycarbonyl)-4-methyl-oxazole is conveniently introduced into the heated reactor in the form of a solution in a suitable organic solvent. Toluene is an especially suitable solvent.

The reaction is advantageously also carried out in the presence of an added inert gas, especially nitrogen.

The process in accordance with the invention can be carried out continuously or in batches, preferably continuously, and advantageously in a packed bed reactor which consists, for example, of one or more thermostabilized columns packed with the catalyst. A tube assembly heat exchanger, of conventional design, is particularly suitable on a production scale. The diameter and the length of the individual tubes is not critical. Conveniently, the diameter is chosen so that a catalyst deactivated by coke deposition can be regenerated by means of an oxygen-containing gas, preferably air. A regeneration of the catalyst by burning off the deposited coke is normally required after using the catalyst for 100 to 200 hours.

50 to 200 g of 5-(lower alkoxycarbonyl)-4-methyl-oxazole/liter catalyst volume/hour (throughflow velocity) are preferably introduced into the reactor. The amounts of ammonia, solvent and inert gas introduced are advantageously chosen so that the concentration of 5-(lower alkoxy-carbonyl)-4-methyl-oxazole does not exceed 10 mol percent.

The process in accordance with the invention yields the desired 5-cyano-4-methyl-oxazole in high purity. For the working-up, the gaseous byproducts are separated from the condensable oxazole as well as from the water and alcohol formed in the reaction, conveniently by cooling. Most of the exhaust gases are preferably re-introduced into the reactor. Thereupon, the organic phase is separated from the resulting two-phase mixture and this is subjected to a rectification.

DESCRIPTION OF THE SPECIFIC EMBODIMENTS

The process in accordance with the invention is illustrated in more detail by the following Examples.

EXAMPLE 1

The reactor consists of a vertically arranged glass tube (length about 30 cm, diameter about 2 cm) which is surrounded by a tube oven and is connected to a condenser. The upper and lower portions of the glass tube are filled with ceramic beads: the middle portion is filled with catalyst (30 ml). Commercially obtainable zirconium oxide catalyst (Harshaw Zr-0304T). which has been calcined at 700° C. for 2 hours prior to use, is used as the catalyst.

The heating of the oven is adjusted to 310° C. and 18 ml of a 25% solution of 5-ethoxycarbonyl-4-methyl-oxazole in toluene, 7 liters of ammonia and 7 liters of nitrogen are introduced into the reactor each hour. The reaction products are condensed in a condenser and analyzed by gas chromatography.

With a conversion of 99% the yield of 5-cyano-4-methyl-oxazole is 78%.

EXAMPLE 2

A commercially obtainable zirconium oxide powder (Dynazirkon®F of Dynamit Nobel), which prior to use was tabletted (3×3 mm) with stearic acid (1 weight percent) as a lubricating agent and subsequently calcined at 700° C. for 3 hours, is used as the catalyst in the reactor described in Example 1.

Using this catalyst, with a conversion of 99% the yield of 5-cyano-4-methyl-oxazole is 75%.

EXAMPLE 3

A zirconium oxide produced from zirconium nitrate is used as the catalyst in the reactor described in Example 1. With a conversion of 96% the yield of 5-cyano-4-methyl-oxazole is 74%.

The catalyst used is produced as follows:

15 mg of microcrystalline cellulose (Avicel pH 101) and 310 ml of 25% aqueous ammonia are added to a stirred solution of 500 g of zirconium nitrate pentahydrate in 2.5 liters of distilled water. The precipitate is filtered off under suction, washed with distilled water and calcined at 700° C. for 3 hours. The resulting zirconium oxide is pulverized and then mixed with 4 percent by weight of stearic acid (lubricating agent), tabletted (diameter 6 mm, thickness 3 mm), and heated at 500° C. for 3 hours.

EXAMPLE 4

A zirconium oxide produced from zirconyl chloride is used as the catalyst in the reactor described in Example 1. With a conversion of 99% the yield of 5-cyano-4-methyl-oxazole is 81%.

The catalyst used is produced as follows:

25 g of graphite and 200 g of 25% aqueous ammonia are added to a stirred solution of 397 g of zirconyl chloride hexahydrate in 1.1 liter of distilled water. The precipitate is filtered off under suction, washed with distilled water, dried at 130° C. for 16 hours, tabletted (diameter 3 mm, thickness 2.2 mm) and calcined at 700° C. for 3 hours.

EXAMPLE 5

A zirconium oxide catalyst coated on aluminum oxide is used in the reactor described in Example 1 and the temperature of the oven is adjusted to 320° C. With a conversion of 98% the yield of 5-cyano-4-methyl-oxazole is 76%.

The catalyst used is produced as follows:

70 g of γ-aluminum oxide (Harshaw Al-111-73R) are heated at 1000° C. for 16 hours and then impregnated with 40.5 g of zirconium nitrate pentahydrate in 40.5 ml of distilled water. After the impregnation the aluminum oxide is heated in a tube oven to 450° C. within 5 hours under passage of a stream of air at a rate of 200 liters/hour and subsequently held at this temperature until nitrous gases are no longer evolved. The coating of the zirconium oxide on the thus-produced catalyst is 15%.

EXAMPLE 6

A hafnium oxide catalyst produced from hafnium oxychloride is used in the reactor described in Example 1. With a conversion of 98% the yield of 5-cyano-4-methyl-oxazole is 82%.

The catalyst used is produced as follows:

200 g of 25% aqueous ammonia are added to a stirred solution of 500 g of hafnium oxychloride octahydrate in 1.4 liters of distilled water. The precipitate is filtered off under suction, washed with distilled water, dried at 130° C. for 16 hours, mixed with 4 g of stearic acid, tabletted and calcined at 600° C. for 3 hours.

EXAMPLE 7

A zirconium oxide catalyst coated on aluminum silicate is used in the reactor described in Example 1, and the temperature of the oven is adjusted to 350° C. With a conversion of 98% the yield of 5-cyano-4-methyl-oxazole is about 65%.

The catalyst used is produced as described in Example 5, but using an aluminum silicate carrier with a specific surface of about 30 m²/g (Norton SA 3232) instead of the aluminium oxide carrier. The coating of the zirconium oxide on the thus-produced catalyst is 9.3% in this case.

EXAMPLE 8

A zirconium oxide catalyst produced from zirconium propylate is used in the reactor described in Example 1. With a conversion of 99% the yield of 5-cyano-4-methyl-oxazole is about 81%.

The catalyst used is produced as follows:

325 ml of distilled water are added to a stirred solution of 525 g of zirconium propylate in 650 ml of ethanol. The resulting mixture is subsequently evaporated on a rotary evaporator and the residue is dried at 150° C. for 16 hours. The resulting zirconium oxide is pulverized and mixed with 8 g of stearic acid, tabletted and calcined at 700° C. for 3 hours.

EXAMPLES 9-14

The procedure described in Example 1 is repeated, but with different ammonia and nitrogen throughflow velocities. The results of these experiments, from which it is evident that the yield depends on these throughflow velocities, are compiled in the following Table:

| Example | Ammonia -throughflow velocity (1/hour) | Nitrogen -throughflow velocity (1/hour) | Conversion (%) | Yield (%) |
| --- | --- | --- | --- | --- |
| 9 | 7 | 14 | 99 | 74 |
| 10 | 7 | — | 99 | 65 |
| 11 | 3.5 | 14 | 95 | 74 |
| 12 | 3.5 | — | 99 | 30 |
| 13 | 1.8 | 7 | 98 | 73 |
| 14 | 0.9 | 7 | 99 | 73 |

I claim:

1. A process for the manufacture of 5-cyano-4-methyl-oxazole, which comprises reacting a 5-(lower alkoxycarbonyl)-4-methyl-oxazole with ammonia, in the gaseous phase, in the presence of a catalyst selected from the group consisting of zirconium oxide and hafnium oxide.

2. A process according to claim 1, in which 5-ethoxycarbonyl-4-methyl-oxazole is used as the 5-(lower alkoxycarbonyl)-4-methyl-oxazole.

3. A process according to claim 1, in which the specific surface of the catalyst, whether undiluted or mixed with an inert carrier, is not less than 10 $m^2/g$.

4. A process according to claim 1, in which the molar ratio of ammonia: 5-(lower alkoxycarbonyl)4-methyl-oxazole is not less than 1.5:1.

5. A process according to claim 4, in which the molar ratio of ammonia to 5-(lower alkoxycarbonyl)-4-methyl-oxazole is 5:1 to 10:1.

6. A process according to claim 1, in which the reaction is effected at a temperature in the range of about 230° C. to 400° C.

7. A process according to claim 6, wherein the reaction is effected at a temperature between about 260° C. and about 350° C.

8. A process according to claim 1, in which the 5-(lower alkoxycarbonyl)-4-methyl-oxazole is introduced into the heated reactor in the form of a solution in an organic solvent.

9. A process according to claim 8, in which the organic solvent is toluene.

10. A process according to claim 1, in which the reaction is carried out in an inert atmosphere.

11. A process according to claim 10, in which the inert atmosphere is gaseous nitrogen.

12. A process according to claim 1, in which the catalyst is undiluted with an inert carrier and has a specific surface in the range of 10 to 40 $m^2/g$.

13. A process according to claim 1, in which the catalyst is diluted with a carrier material and has a specific surface in the range of 10 to 90 $m^2/g$.

14. A process according to claim 1, in which the reaction is carried out under atmospheric pressure.

* * * * *